US006468424B1

(12) United States Patent
Dönig et al.

(10) Patent No.: US 6,468,424 B1
(45) Date of Patent: Oct. 22, 2002

(54) CONNECTOR ADAPTED TO CONNECT A STORAGE CONTAINER FOR SOLUTION INGREDIENTS TO A MEDICAL APPARATUS

(75) Inventors: Rainer Dönig, Frankfurt (DE); Joachim Döpper, Gross-Gerau (DE); Wolfgang Schulz, St. Wendel (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 0 days.

(21) Appl. No.: 09/281,909

(22) Filed: Mar. 31, 1999

(30) Foreign Application Priority Data

Apr. 1, 1998 (DE) .......................... 198 14 687

(51) Int. Cl.[7] ............................. B01D 61/30
(52) U.S. Cl. ................. 210/232; 210/321.71; 235/375; 235/454; 235/462.01
(58) Field of Search ........................ 141/67, 83, 326, 141/346; 210/647, 321.71, 232, 240; 439/488, 489, 491, 955; 235/375, 462.01, 454, 462.02, 462.04; 604/404

(56) References Cited

U.S. PATENT DOCUMENTS

| | | | | |
|---|---|---|---|---|
| 4,869,286 A | * | 9/1989 | Williams et al. | 137/318 |
| 5,311,899 A | * | 5/1994 | Isayama et al. | 137/240 |
| 5,540,265 A | * | 7/1996 | Polaschegg et al. | 210/647 |
| 5,572,992 A | * | 11/1996 | Kankkunen et al. | 128/203.14 |
| 5,583,948 A | * | 12/1996 | Shibayama | 382/141 |
| 5,925,014 A | * | 7/1999 | Teeple, Jr. | 604/51 |
| 5,997,502 A | * | 12/1999 | Reilly et al. | 604/67 |

FOREIGN PATENT DOCUMENTS

| | | |
|---|---|---|
| EP | 0 311 848 A2 | 4/1989 |
| EP | 0 311848 A3 | 4/1989 |
| EP | 0 575 970 A2 | 12/1993 |
| WO | WO 92/11046 | 7/1992 |
| WO | WO 96/25214 | 8/1996 |

\* cited by examiner

Primary Examiner—John Kim
(74) Attorney, Agent, or Firm—Kenyon & Kenyon

(57) ABSTRACT

The present invention relates to a dialysis machine with a device for preparing dialysis solutions. Simple and reliable preparation of dialysis fluids of different concentrations is achieved by the fact that the device has a detector device, at least two connections and at least two interchangeable storage containers to hold the solution ingredients to be metered, each being connected to at least one connector, and with the connectors being connectable to the connections, and with the connectors or the areas of a connecting tube near the connectors having identification means which can be detected by the detector device. The present invention also relates to a connector for connecting a storage container with solution ingredients to a medical apparatus, where the connector or areas of a connecting tube near the connector has identification means. The present invention also relates to a method of detecting a connection of a solution ingredient storage container. A simple and reliable implementation of the method is guaranteed by the fact that the connector is provided with identification means and is attached to a matching component, and a reader unit determines the type and position of the connector.

3 Claims, 2 Drawing Sheets

CONNECTOR ADAPTED TO CONNECT A STORAGE CONTAINER FOR SOLUTION INGREDIENTS TO A MEDICAL APPARATUS

FIELD OF THE INVENTION

The present invention relates to a dialysis machine with a device for preparing dialysis solutions. The present invention also relates to a connector for connecting a storage container to a medical apparatus and to a method of detecting the connection.

BACKGROUND INFORMATION

A generic dialysis machine is disclosed in International Patent Application No. WO 92/11046, for example, which discloses a dialysis machine with a device which prepares dialysis solutions of the desired properties and feeds them into the dialysis fluid circulation of the machine. The required solutions are prepared by using tablets which contain the necessary ingredients of the dialysis solutions and are added as needed to a mixing chamber which holds water and dissolved in the water there. The tablets may be stored in a magazine arranged above the mixing apparatus, for example. A concentration curve of the ingredients of the dialysis solutions adapted to each patient's needs is achieved by adding tablets containing different quantities or types of active ingredients to the dissolving operation at predetermined times and then supplying this solution to the dialysis fluid circulation. To prevent errors in the type and concentration of dialysis solutions administered and to permit monitoring of the process, the tablets have a bar code which can be detected using a reading device on the dialysis machine. One disadvantage of this device is that numerous tablets containing different active ingredient concentrations in accordance with the width of the concentration range to be used must be produced and provided with a bar code, which makes them accordingly complicated and expensive to manufacture. Furthermore, due to the solid nature of the tablets, devices for adding the tablets to a suitable solvent and for dissolving the tablets are necessary, so that the dialysis machines have a relatively complicated design.

SUMMARY OF THE INVENTION

An object of the present invention is to make available a dialysis machine with which dialysis fluids of different concentrations can be reliably prepared.

The present invention provides a dialysis machine with a dialysis solution preparation device including a detector device, at least two connections and at least two interchangeable storage containers to accommodate the solution ingredients to be metered, each container being connected to at least one connector, the connectors being connectable to the connections, and the connectors or the areas of a connecting tube near the connectors having identifiers that can be detected by the detector device. This makes it possible to easily and reliably prepare dialysis solutions of different concentrations, using conventional standard solutions as the starting solutions. Accordingly, this eliminates the need for preparing numerous standard solutions of different concentrations to make it possible to perform dialysis that is optimized to each patient's needs.

According to the present invention, the connectors or the areas of a connecting tube near the connectors have identifiers that can be detected by the detector device. This makes it possible to safely prevent mistakes in allocation of the storage containers to the connections of the device. The dialysis machine automatically detects the type and quantity of solution in each storage container on the basis of the identifiers which identify the storage containers, in such a way that definite identification is always possible regardless of the choice of connection.

The operator of the dialysis machine attaches the connectors of the required storage containers to the connections of the apparatus in any order and, via a control device, for example, inputs the desired concentrations and/or concentration gradients of the dialysis fluid to be prepared. The dialysis machine according to the present invention automatically recognizes on the basis of the identifiers which connection is receiving which solutions, and it performs the desired preparation or mixing operation accordingly through the switching of pumps or valves. It is thus possible to safely avoid confusing the connections, which could endanger the patient, or preparing dialysis solutions with unwanted ingredients or quantities. A further advantage of the device according to the present invention is derived from the fact that only a very few standard solutions are ever required to prepare even a large number of different concentrations of dialysis fluids, thus greatly simplifying the production technology and logistics.

According to a preferred embodiment of the present invention, solution bags are provided as the storage containers, comprising a connecting tube having a connector at the end. The solution bags contain standard solutions, for example, only a small number of which need be made available.

The identifiers may be provided at a predetermined position on the connector, and the detector device may be designed and/or arranged in such a way that not only the type but also the position of the identifiers can be detected. Creating the identifiers on the connector has the advantage that it rules out a mix-up of the storage containers or faulty allocation to the connections regardless of the length or number of connecting tubes. It is much less necessary for the operator to pay attention to which connector is being connected to which connection because the dialysis machine according to the present invention automatically recognizes the connector and the storage container or solvent bag connected to it. In addition, the present invention also provides for the detector device to determine the position of the connector, which makes it possible for the operator to recognize that a connector has not been fully attached to the connection. In that case, the identifiers would be displaced slightly compared with the fully attached position, which is detected by the detector device.

It is especially advantageous if the identifier includes a bar code. Such codes can be produced in large numbers and can be applied to the connectors or the connecting tubes without any problem. In addition, using a bar code not only permits detection of the type of solution connected but also permits detection of a disconnection or a faulty connection of a connector.

In another embodiment of the present invention, the bar code is arranged on the connectors in such a way that the bars of the bar code run around the circumferential direction of the connector. This ensures that twisting of the connector cannot lead to faulty or incorrect detection by the detector device, because the bar code extends over the entire circumference. In addition, this yields the advantage that, in contrast with marks running longitudinally on the connector, the bar code can be detected completely by the detector device.

According to a preferred embodiment of the present invention, the identifier includes information on the type and volume of solution ingredients to be metered from the storage container. This means that not only is it possible to control the parameters of the active ingredients, but also to determine the time after which it may be necessary to change the storage containers. In particular, it is possible that in this case the detector device might detect and indicate to the operator too low a volume of the solution for the pending dialysis to be administered from the storage container as early as at the beginning of the treatment. This makes it possible to avoid having to interrupt the dialysis procedure because the storage containers need to be changed.

According to a preferred embodiment of the present invention, an analyzer unit is provided for connection to the detector device, said analyzer unit being designed in such a way that required values for the quantity and/or parameters of the dialysis solution ingredients accommodated in the storage containers can be stored and compared with the actual values obtained by the detector device. Before the start of the treatment, the person operating the dialysis machine enters the required data for the desired active ingredient concentrations, quantities and gradients, for example, whereupon these values are stored as the required values in the analyzer unit. Then the storage containers are connected to the connections on the device using the connectors, and the detector device determines with the help of the identifiers the type and volume, for example, of the solutions connected. Following this, a desired mixture or a profile of active ingredient concentrations over time can be established in accordance with the specifications of the operator of the machine if the analyzer unit does not detect any deviations between the specifications of the operator and the solutions actually used.

It is especially advantageous if a signaling unit or a cutoff device that can be connected to the analyzer unit are provided. For example, when a connector is improperly connected or the wrong solution ingredients are used, it is possible for a visual or acoustic signal to be delivered or for the cutoff device such as valves to be activated, thus preventing wrong or improperly connected solutions from being administered.

The cutoff device may perform a mechanical and/or electrical cutoff of lines. If the analyzer unit detects a discrepancy between the required and actual values with regard to the type or quantity of active ingredients, the cutoff device is activated in such a way that either a supply line to the dialysis machine is cut off, thus preventing dialysis solution from being delivered to the dialyzer, or it is possible for the electric power supply to the pump of the dialysis circuit, for example, not to be activatable for as long as the analyzer unit detects a lack of correspondence between the required value and the actual value.

Furthermore, the present invention concerns a connector for connecting a storage container with solution ingredients to a medical apparatus. The connector has an identifier to identify it. The identifier may include a bar code. Instead of the bar code, other identifiers also be used, permitting reliable identification of the connector or a storage container connected to it.

It is especially advantageous if the bar code is designed to run around the connector. This affords the advantage that it is not necessary to make sure of a specific rotational position when connecting the connector, because according to the present invention the bar code runs around the entire circumference of the connector. Another advantage of such a design is that, unlike marks running longitudinally on the connector, the circumferential bar code can always be detected completely and reliably by a detector device.

The present invention also concerns a method of detecting a connection of a solution ingredient storage container, where the connector is provided with an identifier and is attached to a matching component, and a reader unit determines the type and position of the connector. In that case, the identifier may comprise a bar code. This affords the advantage that it is no longer possible to mix up the connectors and connections identified according to the present invention. In addition, this permits rapid and reliable detection of a defective connection of the connector to the matching component or of any disconnection that might occur during the dialysis operation.

BRIEF DESCRIPTION OF THE DRAWINGS

Additional advantages and details of the present invention are explained in greater detail below on the basis of an embodiment illustrated in the drawing, in which.

DETAILED DESCRIPTION

Figure 1:
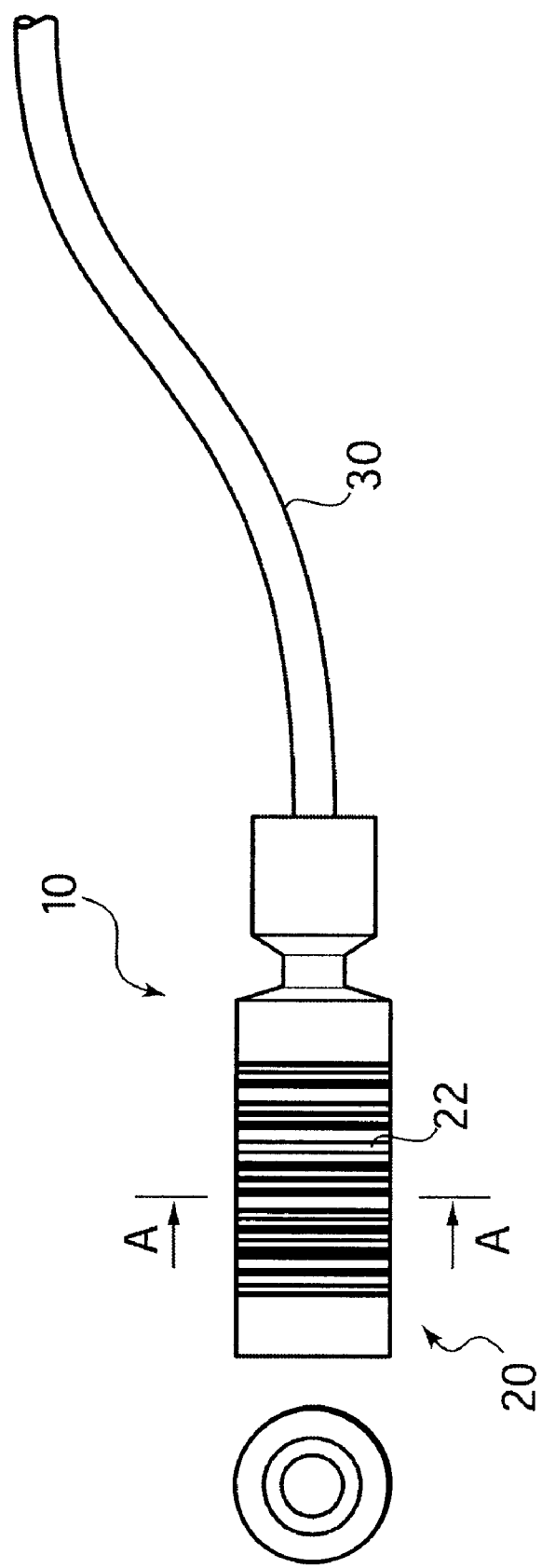
FIG. 1 shows a connector with a bar code arranged on a connecting tube to a solution bag.

FIG. 1 shows connector 10 in a sectional diagram (left) according to line A—A in the side view shown on the right in FIG. 1. Connector 10 is arranged at the end of connecting tube 30, with the connecting tube 30 being connected to a solution bag containing the required solution ingredients at its other end.

Connector 10 has bar code 22 as identifier 20, with the bars of bar code 22 running circumferentially around connector 10. This ensures that, regardless of whether the connector 10 is twisted in attaching it to a connection, detection of bar code 22 by the detector device is still possible.

Bar code 22 contains, for example, information about the type and quantity of the solution held in the solution bag associated with it. After selecting the suitable solutions, the person operating the dialysis machine can attach the connectors to any connections on the dialysis machine because according to the present invention the information of identifier 20 is detected or bar code 22 is read. This method of identifying the solution bag rules out the possibility of mixing up the solutions, which could lead to dispensing incorrectly prepared dialysis fluids. The arrangement of bar code 22 on connector 10 according to FIG. 1 also makes it possible to detect whether connector 10 has been properly and completely attached to the connection on the machine. If this is not the case, the detector device will detect a bar pattern which, because of the displacement, does not correspond completely to the bar pattern detected when connector 10 is properly connected. This permits safe and reliable detection of the faulty connection or any disconnection occurring during operation.

The dialysis machine according to the present invention makes it possible to achieve a higher quality of treatment due to the fact that the dialysis solutions administered, in particular peritoneal dialysis solutions, can be prepared individually and optimized to each patient's needs. In particular, it is possible to use standard solutions, only a relatively small number of which need be provided. Increased convenience and greater safety in operation are thus achieved due to the fact that the solution bags and/or storage containers can be attached to the connections in any order, because the solution bags and their contents can be identified automatically and unambiguously by the device according to the present invention.

Figure 2:
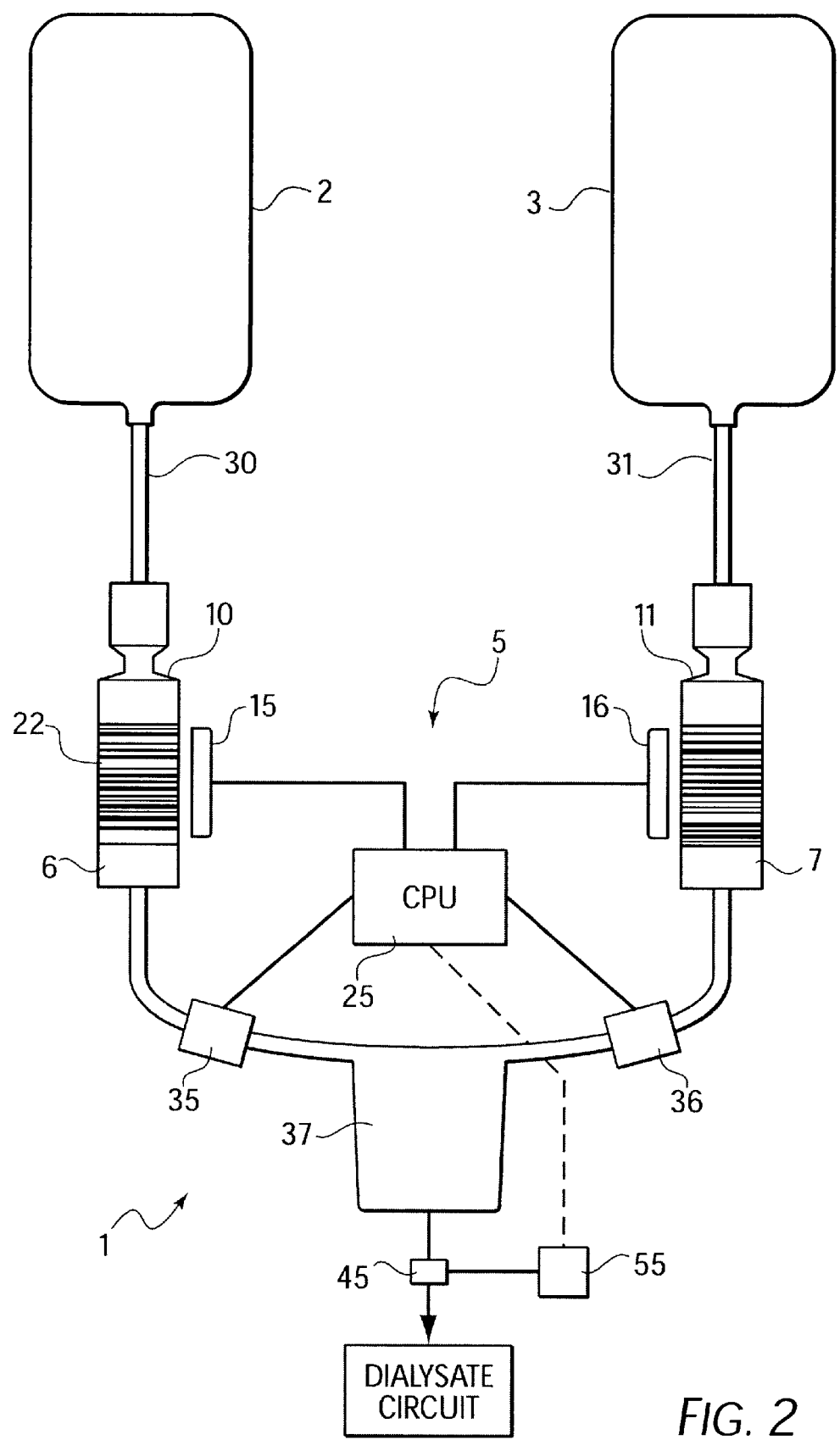
FIG. 2 shows the dialysis machine with a preparation device according to the present invention.

FIG. 2 shows a dialysis machine having a preparation device 1 for preparing a dialysis solution from a first solution bag 2 and a second solution bag 3. The preparation device 1 has a first connection 6 and a second connection 7, although more connections can be provided. The first solution bag has a connecting tube 30 and a connector 10 with a bar code 22. Alternatively, bar code 22 could be placed on connecting tube 30. The second bag 3 is connected by second connecting tube 31 and connector 11 to second connection 7. The preparation device 1 includes a detector device 5 having bar code readers 15 and 16 and control device 25, for example a microprocessor. The control device 25 can control the flow of the solution of solution bag 2 through a valve or flow meter 35 and the flow of the solution of solution bag 3 through valve or flow meter 36 to a mixing chamber 37. An analyzer unit 55 connectable to the detection device 5 is also provided for analyzing the dialysis solution and controlling a cutoff device 45.

What is claimed is:

1. A connector adapted to connect a storage container for solution ingredients to a medical apparatus, the connector being disposed adjacent an outlet of the storage container and comprising an identifier, the identifier comprising a bar code, the identifier indicating a type and quantity of the solution ingredients, the identifier being arranged to indicate a position of the connector to determine incomplete connection to the medical apparatus, wherein the bar code indicates a pattern when the connection is complete, and a different pattern when the connection is incomplete.

2. The connector as recited in claim 1 wherein the bar code extends circumferentially around the identifier.

3. The connector as recited in claim 1 wherein the medical apparatus is a dialysis machine.

* * * * *

(12) EX PARTE REEXAMINATION CERTIFICATE (6919th)
United States Patent
Dönig et al.

(10) Number: US 6,468,424 C1
(45) Certificate Issued: Jul. 7, 2009

(54) CONNECTOR ADAPTED TO CONNECT A STORAGE CONTAINER FOR SOLUTION INGREDIENTS TO A MEDICAL APPARATUS

(75) Inventors: Rainer Dönig, Frankfurt (DE); Joachim Döpper, Gross-Gerau (DE); Wolfgang Schulz, St. Wendel (DE)

(73) Assignee: Fresenius Medical Care Deutschland GmbH, Bad Homburg (DE)

Reexamination Request:
No. 90/008,922, Dec. 12, 2007

Reexamination Certificate for:
Patent No.: 6,468,424
Issued: Oct. 22, 2002
Appl. No.: 09/281,909
Filed: Mar. 31, 1999

(30) Foreign Application Priority Data

Apr. 1, 1998 (DE) .......................... 198 14 687

(51) Int. Cl.
*A61M 1/16* (2006.01)
*A61M 39/10* (2006.01)
*A61M 39/00* (2006.01)

(52) U.S. Cl. .................. 210/232; 210/321.71; 235/375; 235/454; 235/462.01

(58) Field of Classification Search .................. None
See application file for complete search history.

(56) References Cited

U.S. PATENT DOCUMENTS

| | | |
|---|---|---|
| 4,468,222 A | 8/1984 | Lundquist |
| 4,587,407 A | 5/1986 | Ahmed |
| 4,895,657 A | 1/1990 | Polaschegg |
| 4,978,335 A | 12/1990 | Arthur, III |
| 4,990,058 A | 2/1991 | Eslinger |
| 5,056,036 A | 10/1991 | Van Bork |
| 5,344,392 A | 9/1994 | Senninger et al. |
| 5,421,823 A | 6/1995 | Kamen et al. |
| 5,562,836 A | 10/1996 | Joie et al. |
| 5,588,873 A | 12/1996 | Hamai et al. |
| 5,591,344 A | 1/1997 | Kenley |
| 5,658,456 A | 8/1997 | Kenley |
| 5,788,099 A | 8/1998 | Treu |
| 5,925,011 A | 7/1999 | Faict et al. |
| 5,925,014 A | 7/1999 | Teeple |
| 6,017,318 A | 1/2000 | Gauthier et al. |

FOREIGN PATENT DOCUMENTS

| | | |
|---|---|---|
| JP | A 52-144185 | 12/1977 |
| JP | A 3-168373 | 7/1991 |
| JP | A 5-231329 | 9/1993 |
| JP | A 5-508700 | 12/1993 |
| JP | A 8-115767 | 5/1996 |
| JP | A 9-000618 | 1/1997 |

*Primary Examiner*—Krisanne Jastrzab

(57) ABSTRACT

The present invention relates to a dialysis machine with a device for preparing dialysis solutions. Simple and reliable preparation of dialysis fluids of different concentrations is achieved by the fact that the device has a detector device, at least two connections and at least two interchangeable storage containers to hold the solution ingredients to be metered, each being connected to at least one connector, and with the connectors being connectable to the connections, and with the connectors or the areas of a connecting tube near the connectors having identification means which can be detected by the detector device. The present invention also relates to a connector for connecting a storage container with solution ingredients to a medical apparatus, where the connector or areas of a connecting tube near the connector has identification means. The present invention also relates to a method of detecting a connection of a solution ingredient storage container. A simple and reliable implementation of the method is guaranteed by the fact that the connector is provided with identification means and is attached to a matching component, and a reader unit determines the type and position of the connector.

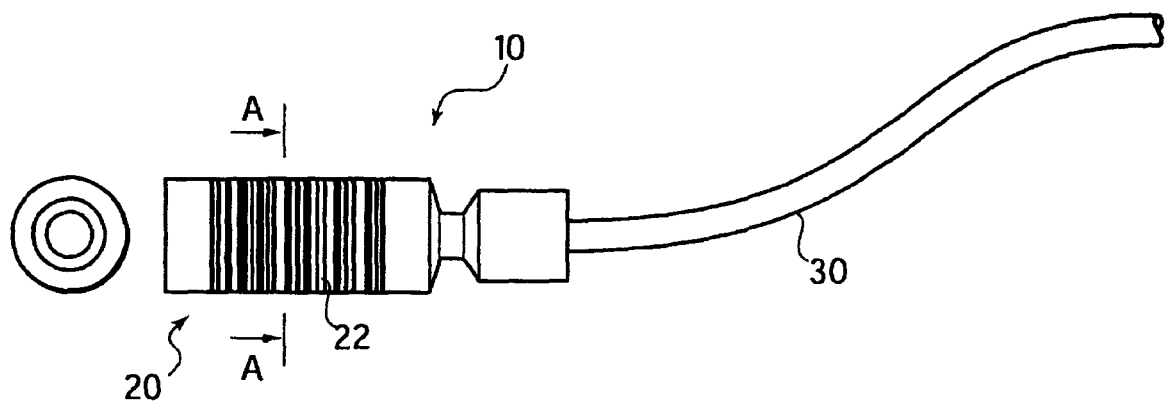

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–3, dependent on an amended claim, are determined to be patentable.

New claims 4–20 are added and determined to be patentable.

1. A connector adapted to connect a storage container for solution ingredients to a medical apparatus, the connector being disposed adjacent an outlet of the storage container and comprising an identifier, the identifier comprising a bar code, the identifier indicating a type and quantity of the solution ingredients, the identifier being arranged to indicate a position of the connector to determine incomplete connection to the medical apparatus, wherein the bar code indicates a pattern *to a detector device* when the connection is complete, and a different pattern when the connection is incomplete.

*4. The connector according to claim 1, wherein the bar code extends circumferentially around the connector.*

*5. The connector according to claim 4, wherein the bar code extends circumferentially around substantially the entire circumference of the connector.*

*6. The connector according to claim 4, wherein the bar code extends circumferentially around the entire circumference of the connector.*

*7. The connector according to any one of claims 1, 4, 5 or 6, wherein a displacement of the bar code relative to the connection to which it is connected causes the pattern detected when the connection is incomplete to be different from the pattern when the connection is complete.*

*8. The connector according to any one of claims 1, 4, 5 or 6, wherein the connector is connected to the storage container via a separate connecting tube, said connecting tube being connected at one end to a neck portion of the storage container, and being connected at an opposite end to the connector.*

*9. The connector according to claim 8, wherein the storage container is a solution bag.*

*10. The connector according to claim 8, wherein the storage container contains a standard dialysis solution.*

*11. The connector according to claim 10, wherein the connector is connected to a connection of a dialysis machine.*

*12. The connector according to claim 11, wherein the bar code is adapted to be readable by a detector device of the dialysis machine.*

*13. The connector according to claim 12, wherein the bar code is adapted to be readable by the detector device of the dialysis machine from multiple positions around the circumference of the connector.*

*14. The connector according to claim 12, wherein the bar code is adapted to be readable by the detector device of the dialysis machine from any position around the circumference of the connector.*

*15. The connector according to claim 9, wherein the storage container contains a standard dialysis solution.*

*16. The connector according to claim 15, wherein the connector is connected to a connection of a dialysis machine.*

*17. The connector according to claim 16, wherein the bar code is adapted to be readable by a detector device of the dialysis machine.*

*18. The connector according to claim 17, wherein the bar code is adapted to be readable by the detector device of the dialysis machine from multiple positions around the circumference of the connector.*

*19. The connector according to claim 17, wherein the bar code is adapted to be readable by the detector device of the dialysis machine from any position around the circumference of the connector.*

*20. The connector of claim 1, wherein the position indicated is an axial position.*

\* \* \* \* \*